(12) United States Patent
Hastings et al.

(10) Patent No.: US 7,993,481 B2
(45) Date of Patent: Aug. 9, 2011

(54) CATHETER WITH EMBEDDED COMPONENTS AND METHOD OF ITS MANUFACTURE

(75) Inventors: John M. Hastings, Minneapolis, MN (US); Alicia A. King, Bloomington, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 733 days.

(21) Appl. No.: 11/646,578

(22) Filed: Dec. 28, 2006

(65) Prior Publication Data

US 2008/0161774 A1 Jul. 3, 2008

(51) Int. Cl.
*A61M 25/16* (2006.01)

(52) U.S. Cl. ............... 156/294; 156/272.2; 604/524

(58) Field of Classification Search ............ 156/272.2, 156/86, 156, 293, 294, 296, 303.1; 604/524
See application file for complete search history.

(56) References Cited

U.S. PATENT DOCUMENTS

| | | | |
|---|---|---|---|
| 4,938,676 A * | 7/1990 | Jackowski et al. | 425/140 |
| 5,395,328 A | 3/1995 | Ockuly et al. | |
| 5,395,329 A | 3/1995 | Fleischhacker et al. | |
| 5,484,425 A * | 1/1996 | Fischell et al. | 604/528 |
| 5,524,337 A * | 6/1996 | Houser et al. | 29/825 |
| 5,700,253 A * | 12/1997 | Parker | 604/526 |
| 5,811,043 A * | 9/1998 | Horrigan et al. | 264/138 |
| 5,891,110 A * | 4/1999 | Larson et al. | 604/523 |
| 5,951,929 A | 9/1999 | Wilson | |
| 6,456,863 B1 | 9/2002 | Levin et al. | |
| 6,554,794 B1 | 4/2003 | Mueller et al. | |
| 6,575,934 B2 | 6/2003 | Duchamp | |
| 6,582,536 B2 | 6/2003 | Shimada | |
| 6,702,972 B1 * | 3/2004 | Markle | 264/230 |
| 2001/0003297 A1 * | 6/2001 | Pedersen et al. | 156/296 |
| 2001/0016702 A1 * | 8/2001 | Benjamin | 604/19 |

* cited by examiner

*Primary Examiner* — Richard Crispino
*Assistant Examiner* — Daniel McNally
(74) *Attorney, Agent, or Firm* — Wiley Rein LLP

(57) ABSTRACT

A method of manufacturing a catheter includes providing an outer shaft having a lumen therethrough and at least one catheter component disposed at least partially within the lumen, placing an inner shaft within the lumen such that the at least one catheter component is located between the shafts, thereby forming a catheter assembly having an outer surface, and applying energy to the catheter assembly to melt at least the outer shaft to bond the outer shaft to the inner shaft. A unitary catheter shaft having the at least one catheter component substantially embedded therein results. The durometer of the outer shaft may differ from the durometer of the inner shaft, such that the catheter shaft varies radially in durometer. The durometer of the catheter shaft may also vary longitudinally. A shaping wire may be provided to form the distal end of the catheter shaft into a desired shape.

23 Claims, 6 Drawing Sheets

CATHETER WITH EMBEDDED COMPONENTS AND METHOD OF ITS MANUFACTURE

BACKGROUND OF THE INVENTION a. Field of the Invention

The instant invention relates to catheters that are used in the human body. In particular, the instant invention relates to a catheter with embedded internal components. The present invention also relates to methods of manufacturing a catheter with embedded internal components.

b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site, for example a site within the patient's heart.

A typical electrophysiology catheter includes an elongate shaft. The shaft includes one or more lumens therethrough. The catheter's internal components will generally be disposed within the lumens and/or routed to the proximal end of the catheter through the lumens. For example, a pull wire to deflect the distal end of the catheter may extend from the distal end of the catheter to the proximal end of the catheter through a pull wire lumen.

An electrophysiology catheter will also generally include one or more electrodes on the distal end of the shaft. The electrodes may be used for ablation, diagnosis, or the like. Each electrode is coupled to a lead wire. The lead wires are generally strung through holes that are pierced in the wall of the catheter shaft. The electrode may then be swaged onto the shaft, covering the hole through which the lead wire extends, and adhesive applied around the edge of the electrode. Typically, all lead wires extend to the proximal end of the shaft through a single, central lumen. Exemplary electrophysiology catheters are disclosed in U.S. Pat. Nos. 5,395,328 and 5,395,329, which are hereby incorporated by reference as though fully set forth herein.

In the typical construction of an electrophysiology catheter described above, it is possible for blood or other fluids to bypass the adhesive seal around the electrode. If this happens, the fluid has a direct path into the catheter through the lead wire hole. This is commonly referred to as "fluid ingress," and is known to cause electrical noise on ECGs and shorts between electrodes.

In the case of deflectable (steerable) catheters, the internal components are forced to move when the catheter is deflected. Over several deflections, lead wires may become tangled, break, or lose their insulative coating as they rub against each other and the wall of the catheter shaft. This, in turn, may lead to reduced efficacy of the electrophysiology catheter.

Furthermore, the lumen must be large enough to house all internal components, such as pull wires, lead wires, signal wires, and the like. However, the outer diameter of the catheter shaft must remain small enough for the catheter to fit within the relatively narrow passages of the patient's vasculature. It is thus necessary to reduce the wall thickness of the catheter shaft, which reduces the stiffness of the shaft, potentially leading to undesirable flexure of the distal end during insertion into the patient's vasculature.

BRIEF SUMMARY OF THE INVENTION

It is desirable to embed the internal components of an electrophysiology catheter in the wall of the catheter shaft in order to mechanically isolate and electrically insulate the components from each other.

It is further desirable to provide an electrophysiology catheter that exhibits improved durability without sacrificing deflectability.

In some embodiments, it is desirable to provide an electrophysiology catheter having increased stiffness.

Disclosed herein is a method of manufacturing a catheter, including the steps of: providing an outer shaft having a lumen therethrough and at least one catheter component disposed at least partially within the lumen; placing an inner shaft within the lumen such that the at least one catheter component is located between an inner surface of the outer shaft and an outer surface of the inner shaft, thereby forming a catheter assembly having an outer surface; and applying energy to the catheter assembly to melt at least the outer shaft, whereby the outer shaft bonds to the inner shaft to form a catheter shaft having the at least one catheter component substantially embedded therein. Optionally, the catheter assembly both the outer shaft and the inner shaft may be melted via the application of energy. The energy applied may be thermal energy, radio frequency (RF) energy, or any other energy suitable to melt at least the outer shaft and bond the outer shaft to the inner shaft. In at least some embodiments of the invention, the energy is applied to the outer surface of the catheter assembly.

The outer shaft may include a plurality of segments that are bonded together during subsequent processing (e.g., via the application of energy to the catheter assembly). The segments may differ in durometer, such that the resulting catheter shaft varies longitudinally in durometer.

The inner shaft may be solid or tubular, including a lumen therethrough. Where the inner shaft is tubular, the inner shaft may be supported by a mandrel or a pressure source during melt processing (e.g., the application of energy to the catheter assembly) in order to retain the inner diameter of the catheter assembly. A shaping wire, preferably made of a shape memory alloy, may be disposed within the lumen of the inner shaft to shape at least a portion of the catheter shaft into a curve. To retain the outer diameter of the catheter assembly during melt processing, a heat shrink tube may be placed around the outer shaft prior to melt processing. Alternatively, melt processing may be carried out with the catheter assembly in a mold.

The durometer of the outer shaft may differ from the durometer of the inner shaft, such that the catheter shaft varies radially in durometer. Preferably, the durometer of the inner shaft is greater than the durometer of the outer shaft, as a high durometer inner shaft increases the overall moment of inertia of the shaft.

Typically, at least one of, and preferably both of, the inner and outer shafts is made of a polymeric material. Suitable polymeric materials include, without limitation, polyether block amides, nylon, urethane, polyethylene, Pebax®, and other thermoplastic elastomers.

The internal components embedded into the catheter wall may include lead wires, steering mechanisms, pull wires, temperature sensors (e.g., thermistors and thermocouples), shaping wires, ablation elements, energy delivery wires, signal wires, and compression coils.

According to another aspect of the invention, a method of manufacturing a catheter includes the steps of: providing an outer shaft having a generally circular cross section, a central lumen, and at least one catheter component disposed at least partially within the central lumen; inserting an inner shaft within the central lumen such that the at least one catheter component is located between an outer surface of the inner shaft and an inner surface of the outer shaft, thereby forming a catheter assembly; and heating the outer surface of the catheter assembly to melt at least the outer shaft, whereby the outer shaft bonds to the inner shaft to form a catheter shaft having the at least one catheter component substantially embedded therein. Optionally, the catheter assembly may be placed within a shape retention structure, such as a heat shrink tube or a mold, to retain the generally outer cross section of the catheter assembly during the heating step.

One embodiment of the catheter disclosed herein includes: an inner shaft, an outer shaft made of a melt processing polymer, and at least one catheter component embedded in a wall of the catheter. The wall results from a melting process that bonds the inner shaft and the outer shaft such that the at least one catheter component is substantially surrounded by melt processing polymer. Typically, the at least one catheter component will be coated with a material that resists bonding to the melt processing polymer.

Also disclosed is a catheter formed by the process including the steps of: providing an outer shaft having a lumen therethrough and at least one catheter component disposed at least partially within the lumen, wherein the outer shaft includes an inner surface and an outer surface; placing an inner shaft having an outer surface within the lumen such that the at least one catheter component is located between the inner surface of the outer shaft and the outer surface of the inner shaft; and applying energy to the outer surface of the outer shaft to melt the outer shaft and the inner shaft together, whereby a unitary catheter shaft is formed having the at least one catheter component embedded therein.

An advantage of the present invention is that the embedded components reduce the need for a hollow shaft, thereby permitting a thicker wall and improving the catheter's hoop stiffness, which is often desirable when inserting the catheter into a patient's vasculature.

Another advantage of the present invention, particularly in connection with deflectable catheters, is an improved ability to retain mechanical and electrical integrity over multiple deflection cycles.

Still another advantage of the present invention is that, by embedding the internal components, the likelihood of fluid ingress is greatly reduced.

Yet another advantage of the present invention is that, by embedding the internal components, the amount of electrical noise is reduced.

The foregoing and other aspects, features, details, utilities, and advantages of the present invention will be apparent from reading the following description and claims, and from reviewing the accompanying drawings.

DETAILED DESCRIPTION OF THE INVENTION

The present invention provides a catheter having internally embedded components and methods of manufacturing the same. For purposes of description, the present invention will be described and illustrated in connection with a spiral mapping catheter, such as the Livewire Spiral HP™ catheters of St. Jude Medical, Inc. It is contemplated, however, that the described features and methods may be incorporated into any number of catheters, as would be appreciated by one of ordinary skill in the art.

Figure 1:
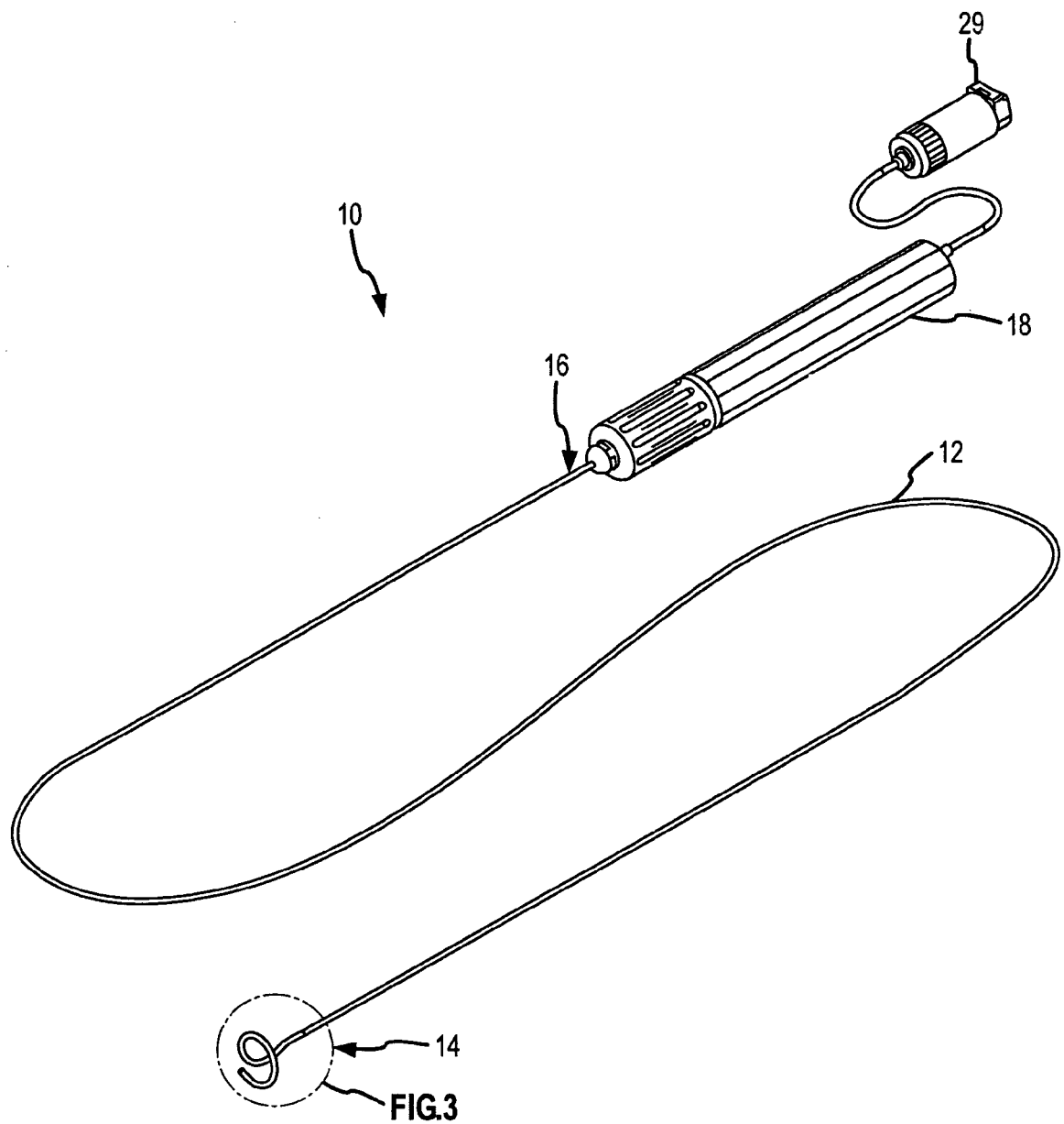
FIG. 1 is a perspective view of a catheter according to an embodiment of the present invention.

Referring now to the figures, and in particular to FIG. 1, an electrophysiology catheter 10 includes a shaft 12 having a distal end 14 and a proximal end 16. A handle 18 may be coupled to proximal end 16 of shaft 12 to control catheter 10.

Figure 2:
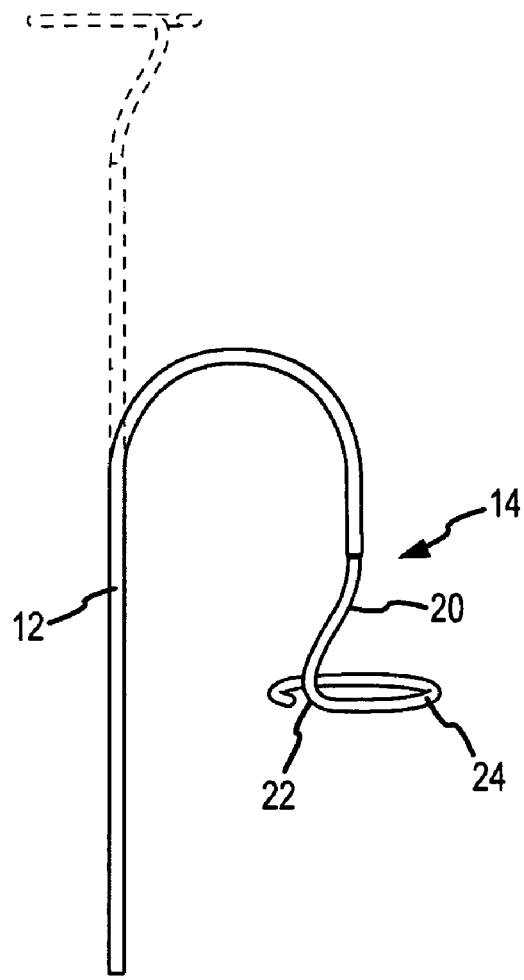
FIG. 2 depicts a deflectable electrophysiology catheter.

As best shown in FIG. 2, shaft 12 may be deflected from a generally straight configuration, shown in phantom, into one or more curved configurations. Deflectability may be provided by one or more steering wires or pull wires (not shown) extending through shaft 12 as generally known in the art. Typically, catheter 10 will be inserted into a patient in the generally straight configuration. By selectively deflecting catheter 10, a physician can navigate distal end 14 thereof through the patient's vasculature to a desired location for treatment or diagnosis. Suitable actuators for the steering wires may be incorporated into handle 18 to permit the physician to selectively deflect distal end 14 of catheter 10 while navigating it through the patient's vasculature. Alternatively, it is also contemplated that one or more guiding introducers may be used to position distal end 14 of catheter 10 at a desired location for treatment or diagnosis.

Distal end 14 of catheter 10 includes a first curved section 20 of shaft 12, a second curved section 22 of shaft 12, and a third curved section 24 of shaft 12. In the embodiment illustrated, first, second, and third curved sections 20, 22, and 24 are unitarily formed, though it is contemplated that they may be separately formed and joined together thereafter.

Figure 3:
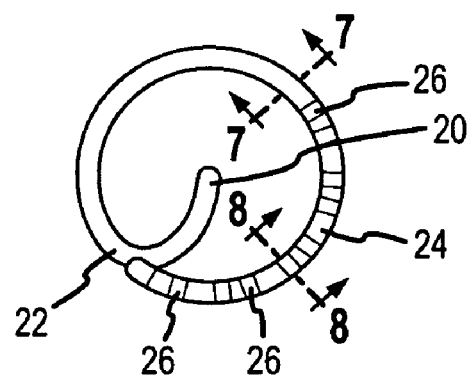
FIG. 3 is a detailed view of the distal end of the electrophysiology catheter of FIG. 2.

Third curved section 24 defines an active region of distal end 14 used in a diagnostic or therapeutic electrophysiology procedure, such as a mapping procedure. As best illustrated in FIG. 3, third curved section 24 is shaped in a circular, nearly closed "C" shape. First and second curved sections 20, 22 tie third curved section 24 to shaft 12 such that a longitudinal axis of shaft 12 would pass roughly through the center of the "C" shape formed by third curved section 24. During insertion of catheter 10 into the patient, the various curved sections 20, 22, 24 may be straightened using a sheath, stylet, or other straightening device (not shown). Of course, distal end 14 may have other geometries without departing from the spirit and scope of the present invention.

To shape curved sections 20, 22, 24, a shaping wire 25 (FIGS. 7 and 8) may be provided extending through at least a portion of shaft 12, such as one or more of curved sections 20, 22, 24. In the present invention, shaping wire 25 helps distal end 14 assume and hold the shape of curved portions 20, 22, 24, such that, when the straightening device is removed, distal end 14 returns to the curved configuration. Shaping wire 25 is preferably a shape memory wire, for example a wire comprising an alloy of nickel and titanium (known commercially as NiTi or Nitinol), which helps distal end 14 of catheter 10 retain a desired shape. Alternatively, shaping wire 25 could be a strip of stainless steel or another resilient metal, or it could be a plastic material.

The terms "shape memory wire" and "shaping wire" are used herein to describe a strip of material (e.g., a circular or flat wire) that, after deformation, will return to its former shape. Thus, shape memory wire is wire that has been deformed to a certain shape and briefly heated to fix that shape. The wire possesses a memory causing it to return to its fixed shape after being deformed. If the wire returns to its former shape without first being heated to a certain transition temperature, it may be referred to as a "superelastic shaping wire". Both superelastic and non-superelastic materials are contemplated for use as shaping wire 25.

In the context of electrophysiology catheters, a plurality of electrodes 26 are positioned around the circumference of third curved section 24. Electrodes 26 may measure electrophysiology information from the surface of the heart. Each electrode 26 is coupled to a corresponding lead wire 28 (FIGS. 4-8). Lead wires 28 extend from distal end 14 to proximal end 16, where they are coupled via plug 29 (FIG. 1) to a suitable system, such as an ECG (not shown) to process the measured electrophysiology information. It is also contemplated that electrodes 26 may be adapted to deliver ablative energy to the surface of the heart in order to lesion tissue, in which case they may be coupled to a suitable source of ablative energy.

Figure 9:
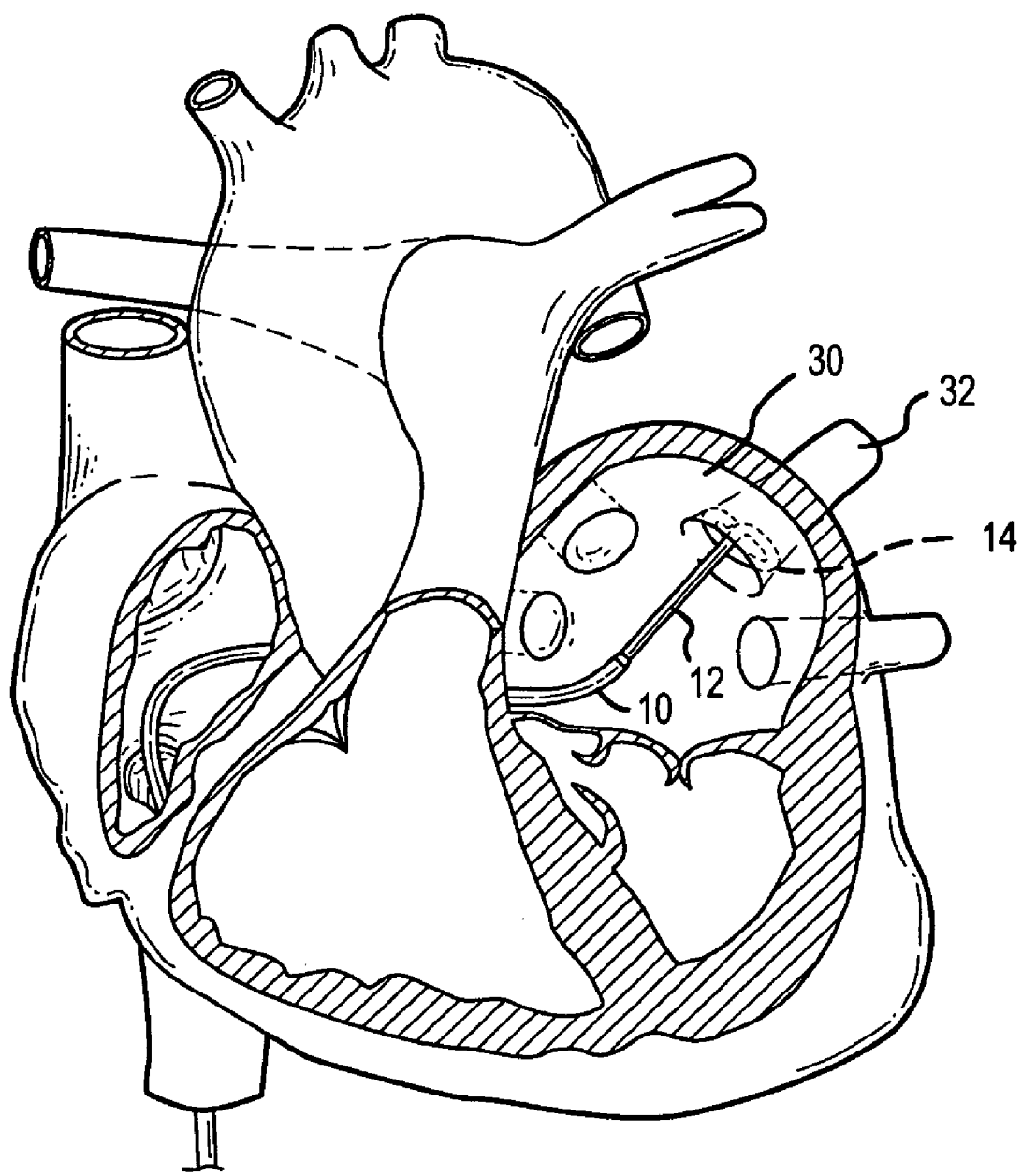
FIG. 9 depicts an electrophysiology catheter inserted into a pulmonary vein.

A typical use of catheter 10 is illustrated in FIG. 9. Catheter 10 has been introduced into the left atrium 30 in order to perform an electrophysiological procedure, such as an electrophysiological mapping, proximate the left superior pulmonary vein 32. As should be clear from FIG. 9, the curvature of third curved section 24 conforms generally to the circumference of the left superior pulmonary vein 32. Further, since the axis of shaft 12 is approximately centered within curved section 24, it is less likely to press against the wall of left superior pulmonary vein 32 during the procedure.

The basic method of manufacture of catheter 10, and in particular of at least a portion of shaft 12, will be described with reference to the embodiment of the invention depicted in FIGS. 4-6. The various components shall be referred to collectively as catheter assembly 100. Reference will also be made to shaft 12; it is contemplated that all or part of shaft 12, such as distal end 14, and in particular curved sections 20, 22, 24, may be manufactured as described herein.

Figure 4:
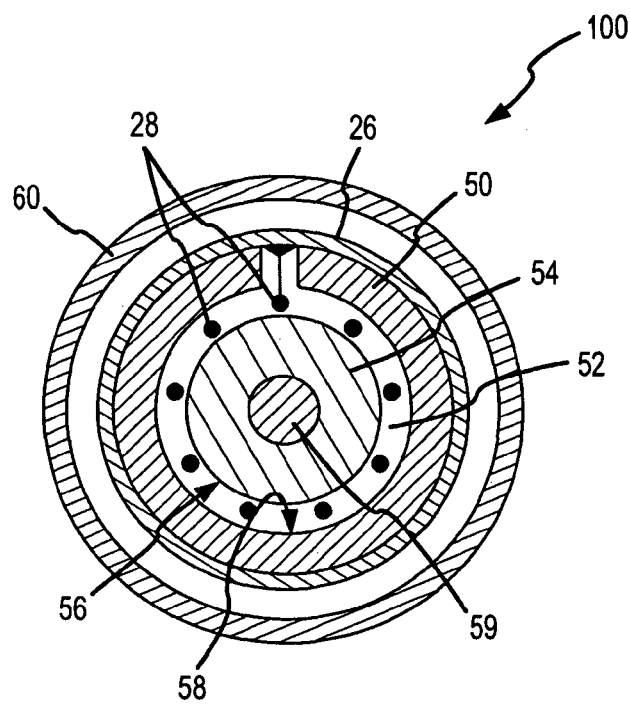
FIG. 4 is a cross section of a catheter assembly prior to processing of the components via heating.

As shown in FIG. 4, which is a cross section of distal end 14 of shaft 12 at an early stage of manufacture, one component of catheter 10 is an outer shaft 50, preferably having a generally circular outer cross section. Outer shaft 50 has a lumen 52 therethrough. Lumen 52 is typically centrally located within outer shaft 50, such that the wall thickness of outer shaft 50 is generally constant around its circumference, but it is within the spirit and scope of the present invention to offset a longitudinal axis of lumen 52 from a longitudinal axis of outer shaft 50.

Outer shaft 50 is typically a melt-processing polymeric material such as polyether block amides, nylon, urethane, polyethylene, and other thermoplastic elastomers. One such elastomer is Pebax®, made by Arkema, Inc. Pebax® of various durometers may also be used, including, without limitation, Pebax® 30D to Pebax® 70D. It is also contemplated for outer shaft 50 to include more than one layer, for example two or more layers of melt-processing polymeric material, which may vary radially in hardness. That is, a first, inner layer of outer shaft 50 may have a first hardness, while a second, outer layer of outer shaft 50 may have a second hardness. Preferably, if a radially-varying outer shaft 50 is utilized, the second, outer layer of outer shaft 50 has a lower hardness than the first, inner layer of outer shaft 50.

Figure 10:
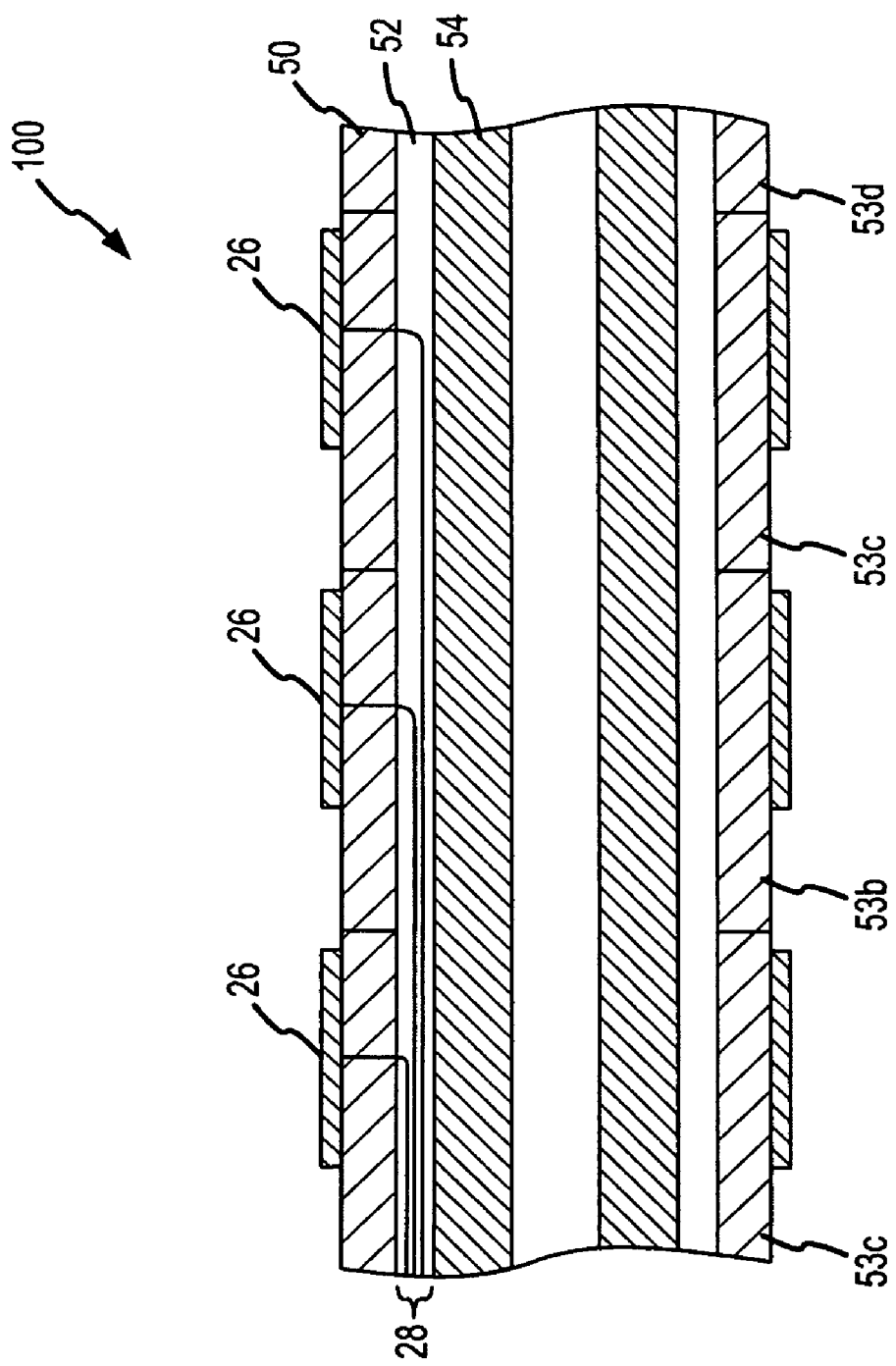
FIG. 10 is a side view, partially cut away, of a catheter assembly prior to lamination via melt processing.

As illustrated in FIG. 10, it is also contemplated that outer shaft 50 may be composed of multiple segments, such as segments 53a, 53b, 53c, 53d, which may vary in hardness and in length. Preferably, the hardness of outer shaft 50 will decrease distally. Thus, most proximal segment 53a has a greater hardness than segment 53b, which has a greater hardness than segment 53c, which has a greater hardness than most distal segment 53d. The length of the segments also preferably decreases distally. The various segments 53a, 53b, 53c, 53d will be bonded together in subsequent processing, resulting in a shaft 12 that has longitudinally varying stiffness, which may be desirable in certain applications of catheter 10.

As described above, electrodes 26 are positioned on the outside of outer shaft 50, and lead wires 28 extend generally longitudinally through lumen 52. This should be familiar to those of ordinary skill, as electrophysiology catheters having a central lumen through which electrode lead wires are routed are known. It will suffice here to reiterate that, as shown in FIG. 10, lead wires 28 are routed through the wall of outer shaft 50 and coupled to corresponding electrodes 26. It is contemplated that lead wires 28 may be coated with an insulation that does not adhere to the polymeric material from which outer shaft 50 is made and in which lead wires 28 will be embedded.

An inner shaft 54 is then placed within lumen 52 such that lead wires 28 are located between an outer surface 56 of inner shaft 54 and an inner surface 58 of outer shaft 50. Preferably, inner shaft 54 is a polymeric material, such as any of the polymeric materials described above in connection with outer shaft 50. As shown in FIG. 10, lead wires 28, only three of which are depicted, extend generally longitudinally along the length of catheter assembly 100, and are freely disposed within lumen 52 of outer shaft 50.

Inner shaft 54 may have a higher melting temperature than outer shaft 50. Inner shaft 54 may also have a durometer that differs from the durometer of outer shaft 50. Preferably, the durometer of inner shaft 54 is higher than the durometer of outer shaft 50, which increases the stiffness of shaft 12. The durometer of inner shaft 54 and outer shaft 50 may both be between about 30D and about 70D. One of ordinary skill in the art will appreciate how to select materials of appropriate durometer for inner shaft 54 and outer shaft 50 for a particular application of catheter 10.

In one preferred embodiment of the invention, inner shaft 54 is tubular, having a central lumen therethrough. It is desirable to maintain the central lumen of inner shaft 54, for example to provide a passageway for shaping wire 25. Thus, a mandrel 59 may be inserted to support inner shaft 54 and retain its inner diameter during subsequent processing. Mandrel 59 may be treated such that it can be easily removed after melt processing, for example by coating mandrel 59 with TEFLON®. As an alternative to mandrel 59, the inner diameter of inner shaft 54 may be supported with a pressurized fluid supplied by a pressure source (not shown). Inner shaft 54 may also be solid (i.e., without a central lumen). A solid inner shaft 54 will increase the stiffness of shaft 12, which may be desirable in certain applications of catheter 10.

A heat shrink tube 60 may be placed around outer shaft 50. Heat shrink tube 60 is preferably a fluoropolymer or polyolefin material such as fluoroethylkene polymer (FEP). As discussed in further detail below, heat shrink tube 60 acts to retain the outer diameter of catheter assembly 100 during subsequent processing. As an alternative to heat shrink tube 60, catheter assembly 100 may be placed into a suitable mold prior to subsequent processing. Either heat shrink tube 60 or the mold may be generally referred to as a "shape retention structure," so named because it retains the overall shape of catheter assembly 100 (that is, the generally circular outer cross section) during melt-processing.

Thus, catheter assembly 100 includes outer shaft 50, electrodes 26, lead wires 28, inner shaft 54, mandrel 59, and heat shrink tube 60. FIG. 4 depicts a cross section of catheter assembly 100 prior to processing (e.g., lamination) of the various components via the application of energy (e.g., heating).

Figure 5:
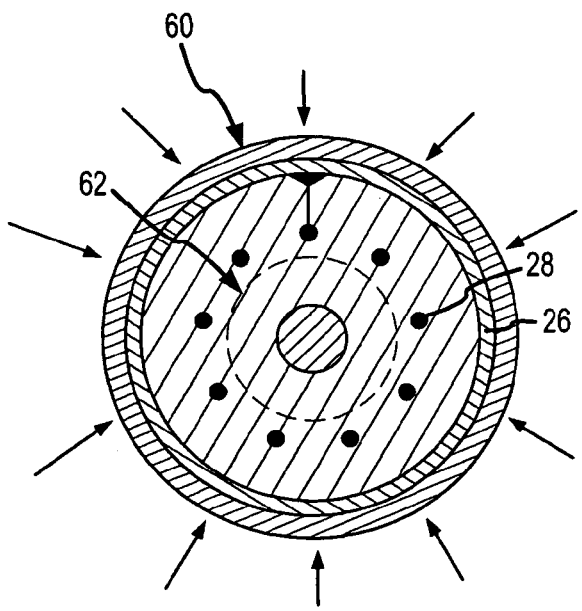
FIG. 5 is a cross section of a catheter assembly during processing.

As shown in FIG. 5, catheter assembly 100 is then melt-processed. Energy is applied to catheter assembly 100, and preferably to the outer surface of catheter assembly 100, to melt at least outer shaft 50, and preferably both outer shaft 50 and inner shaft 54. The energy applied may be thermal energy, radio frequency (RF) energy, or any other energy suitable to melt at least outer shaft 50. Heat shrink tube 60 has a higher melting temperature than outer and inner shafts 50, 54, such that, during the melting process, heat shrink tube 60 will contract while retaining its tubular shape. The combination of applied energy and pressure exerted by heat shrink tube 60 forces melted outer and inner shafts 50, 54 to flow and redistribute about the circumference of catheter assembly 100 and melt together, represented by interface line 62, which substantially surrounds and encapsulates lead wires 28.

Catheter assembly 100 may then be cooled such that outer and inner shafts 50, 54 solidify, thereby forming a unitary catheter shaft 12 with lead wires 28 substantially embedded therein. The term "substantially embedded" contemplates that lead wires 28 may not be surrounded by the material of catheter shaft 12 in their entirety. For example, the proximal ends of lead wires 28 may be free in order to permit coupling into plug 29.

The melt-processing described above may be referred to as "reverse reflow bonding". In contrast to "reflow bonding," which starts with a fixed inner diameter and adds components externally prior to melt-processing, reverse reflow bonding starts with a fixed outer diameter (e.g., outer shaft 50) and adds components internally (e.g., lead wires 28 and inner shaft 54) prior to melt-processing.

Figure 6:
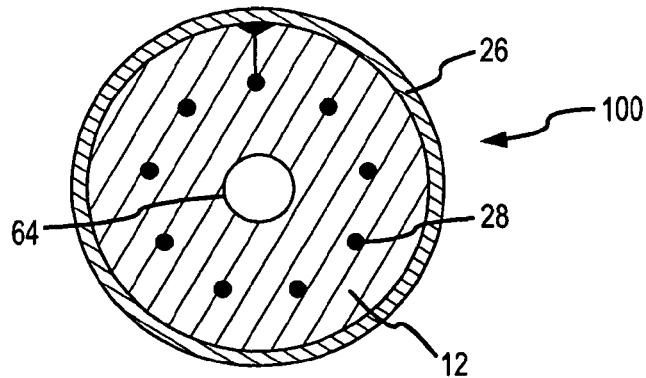
FIG. 6 is a cross section of a catheter assembly after processing.
Figure 7:
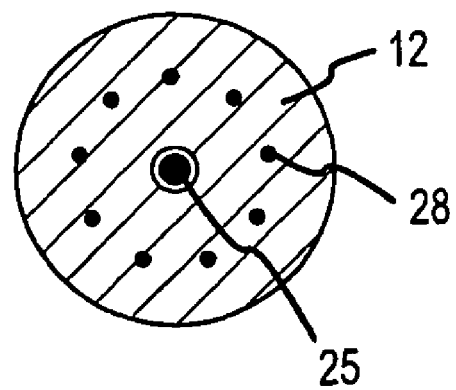
FIG. 7 is a cross section taken along line 7-7 in FIG. 3.
Figure 8:
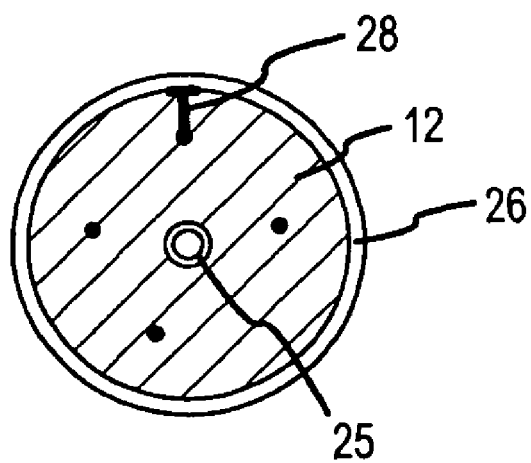
FIG. 8 is a cross section taken along line 8-8 in FIG. 3.

FIG. 6 depicts catheter assembly 100 after the reverse reflow bonding process. Heat shrink tube 60 and mandrel 59 have been removed, resulting in catheter shaft 12 with lead wires 28 substantially embedded therein and extending from distal end 14 to proximal end 16, generally straight along the length of shaft 12. The removal of mandrel 59 leaves behind a central lumen 64, which generally corresponds to the central lumen of inner shaft 54, through which shaping wire 25 may be disposed as shown in FIGS. 7 and 8. Optionally, heat shrink tube 60 and/or mandrel 59 may be left in place after the reverse reflow bonding process.

Advantageously, lead wires 28 are substantially embedded within shaft 12. This is best shown in the cross sections of FIGS. 7 and 8. As seen in FIGS. 7 and 8, each lead wire 28 is mechanically and electrically isolated from all other lead wires 28. This prevents lead wires 28 from becoming entangled, and greatly reduces the amount of electrical noise and the likelihood of shorts between lead wires 28. In addition, the mechanical protection afforded by embedding lead wires 28 within shaft 12 increases the resistance of lead wires 28 to breakage over multiple deflection cycles of shaft 12.

As shown in FIG. 8, embedding lead wires 28 into shaft 12 also advantageously seals the interface between electrode 26 and its corresponding lead wire 28. This substantially reduces the likelihood of fluid ingress, which in turn reduces the likelihood of electrical noise and shorts.

Furthermore, by embedding lead wires 28 in shaft 12, there is a greatly reduced need for a large central lumen 64 within shaft 12. This may result in an increased stiffness of shaft 12 without the need to increase the outer diameter or reduce the number of internal components routed through shaft 12. Indeed, embedding lead wires 28 in shaft 12 may completely eliminate the need for a central lumen 64 through shaft 12.

Catheter 10 formed using the methods of this invention may have varying sizes and various uses. For example, catheter 10 may be used in atrial fibrillation cases as well as atrial tachycardia cases. In connection with certain cardiac applications, catheter 10 is preferably less than about 12 French outer diameter, and more preferably less than about 10 French outer diameter.

Although some embodiments of this invention have been described above with a certain degree of particularity, those skilled in the art could make numerous alterations to the disclosed embodiments without departing from the spirit or scope of this invention. For example, the methods disclosed herein are useful in manufacturing catheters of all types, shapes, and sizes having internal components; the utility of the methods disclosed herein is not limited to the catheter depicted in FIG. 1 and described above.

Furthermore, though the reverse reflow process has been described in connection with embedding electrode lead wires within the catheter shaft, it should be understood that the reverse reflow process may be used to embed any internal catheter component, including, without limitation, steering wires, pull rings, signal wires, energy delivery wires, temperature sensors (e.g., thermocouples and thermistors), shaping wires, ablation elements, and compression coils.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of manufacturing a catheter, comprising:
providing an outer shaft having a lumen therethrough and at least one catheter component disposed at least partially within the lumen;
after the step of providing an outer shaft having a lumen therethrough and at least one catheter component disposed at least partially within the lumen, placing an inner shaft within the lumen such that the at least one catheter component is located between an inner surface of the outer shaft and an outer surface of the inner shaft, thereby forming a catheter assembly having an outer surface; and
after the step of placing an inner shaft within the lumen such that the at least one catheter component is located between an inner surface of the outer shaft and an outer surface of the inner shaft, applying energy to the catheter assembly to melt at least the outer shaft, whereby the outer shaft bonds to the inner shaft to form a catheter shaft having the at least one catheter component substantially embedded therein.

2. The method according to claim 1, wherein the inner shaft includes a lumen therethrough.

3. The method according to claim 2, further comprising:
inserting a mandrel into the lumen of the inner shaft prior to the step of applying energy, whereby the mandrel retains an inner diameter of the catheter assembly during the step of applying energy; and
removing the mandrel after the step of applying energy.

4. The method according to claim 2, further comprising internally pressurizing the lumen of the inner shaft during the step of applying energy such that an inner diameter of the catheter assembly is retained during the step of applying energy.

5. The method according to claim 2, further comprising disposing a shaping wire within the lumen of the inner shaft, whereby the shaping wire forms at least a portion of the catheter shaft into a curve.

6. The method according to claim 1, wherein a durometer of the outer shaft differs from a durometer of the inner shaft.

7. The method according to claim 6, wherein the durometer of the inner shaft is greater than the durometer of the outer shaft.

8. The method according to claim 1, wherein at least one of the outer shaft and the inner shaft comprises a polymeric material.

9. The method according to claim 8, wherein the polymeric material is selected from the group consisting of urethane, poly ether block amide, nylon, polyethylene, and any combination thereof.

10. The method according to claim 1, wherein the outer shaft comprises a plurality of segments, and wherein the plurality of segments are bonded together during the step of applying energy.

11. The method according to claim 10, wherein a first segment of the plurality of segments has a first durometer and a second segment of the plurality of segments has a second durometer, the first durometer differing from the second durometer.

12. The method according to claim 1, wherein the step of applying energy to the catheter assembly to melt at least the outer shaft comprises applying energy to the catheter assembly to melt both the outer shaft and the inner shaft, whereby the outer shaft and inner shaft bond to form a catheter shaft having the at least one catheter component substantially embedded therein.

13. The method according to claim 1, wherein the step of applying energy to the catheter assembly comprises applying thermal energy to the catheter assembly.

14. The method according to claim 1, wherein the step of applying energy to the catheter assembly comprises applying radio frequency energy to the catheter assembly.

15. The method according to claim 1, wherein the step of applying energy to the catheter assembly comprises applying energy to the outer surface of the catheter assembly.

16. The method according to claim 1, further comprising:
placing a heat shrink tube around the outer shaft prior to the step of applying energy, whereby the heat shrink tube retains an outer diameter of the catheter assembly during the step of applying energy; and
removing the heat shrink tube after the step of applying energy.

17. The method according to claim 1, wherein the step of applying energy to the catheter assembly is carried out with the catheter assembly in a mold, whereby the mold retains an outer diameter of the catheter assembly during the step of applying energy.

18. The method according to claim 1, wherein the at least one catheter component is selected from the group consisting of lead wires, steering mechanisms, temperature sensors, shaping wires, ablation elements, energy delivery wires, and compression coils.

19. A method of manufacturing a catheter, the method comprising:
providing a outer shaft having a generally circular outer cross section, a central lumen, and at least one catheter component disposed at least partially within the central lumen;
after the step of providing a outer shaft having a generally circular outer cross section, inserting an inner shaft within the central lumen such that the at least one catheter component is located between an outer surface of the inner shaft and an inner surface of the outer shaft, thereby forming a catheter assembly; and
after the step of inserting an inner shaft within the central lumen such that the at least one catheter component is located between an outer surface of the inner shaft and an inner surface of the outer shaft, heating the outer surface of the catheter assembly to melt at least the outer shaft, whereby the outer shaft bonds to the inner shaft to form a catheter shaft having the at least one catheter component substantially embedded therein.

20. The method according to claim 19, further comprising inserting the catheter assembly into a shape retention structure prior to the step of heating, whereby the shape retention structure retains the generally circular outer cross section during the heating step.

21. The method according to claim 20, wherein the shape retention structure comprises a heat shrink tube, further comprising removing the heat shrink tube after the heating step.

22. The method according to claim 20, wherein the shape retention structure comprises a mold.

23. The method according to claim 19, wherein the inner shaft comprises a substantially solid inner shaft.

* * * * *